US012558562B2

(12) United States Patent
Johnson et al.

(10) Patent No.: US 12,558,562 B2
(45) Date of Patent: Feb. 24, 2026

(54) BATTERY POWERED SYSTEMS FOR LIGHT THERAPY AND RELATED METHODS

(71) Applicant: BioPhotas, Inc., Anaheim, CA (US)

(72) Inventors: Patrick Lamberth Johnson, Santa Ana, CA (US); Roger Allen Gibson, Lake Forest, CA (US)

(73) Assignee: BioPhotas, Inc., Tustin, CA (US)

( * ) Notice: Subject to any disclaimer, the term of this patent is extended or adjusted under 35 U.S.C. 154(b) by 325 days.

(21) Appl. No.: 18/118,988

(22) Filed: Mar. 8, 2023

(65) Prior Publication Data

US 2023/0364440 A1      Nov. 16, 2023

Related U.S. Application Data

(63) Continuation-in-part of application No. 17/162,966, filed on Jan. 29, 2021, which is a continuation of
(Continued)

(51) Int. Cl.
A61N 5/06 (2006.01)

(52) U.S. Cl.
CPC ............ A61N 5/06 (2013.01); A61N 5/0613 (2013.01); A61N 5/0616 (2013.01); *A61N 5/0601* (2013.01); *A61N 2005/0626* (2013.01); *A61N 2005/0632* (2013.01); *A61N 2005/0642* (2013.01); *A61N 2005/0643* (2013.01); *A61N 2005/0645* (2013.01); *A61N 2005/0652* (2013.01); *A61N 2005/0659* (2013.01); *A61N 2005/0663* (2013.01)

(58) Field of Classification Search
CPC ...... A61N 5/06; A61N 5/0613; A61N 5/0616;
A61N 5/0601; A61N 2005/0626; A61N 2005/0632; A61N 2005/0642; A61N 2005/0643; A61N 2005/0645; A61N 2005/0652; A61N 2005/0659; A61N 2005/0663; A61N 2005/0651
See application file for complete search history.

(56) References Cited

U.S. PATENT DOCUMENTS

| | | |
|---|---|---|
| 5,000,752 A | 3/1991 | Hoskin et al. |
| D337,642 S | 7/1993 | Yamasaki et al. |
| (Continued) | | |

FOREIGN PATENT DOCUMENTS

| | | | | |
|---|---|---|---|---|
| WO | WO 2011/001344 A2 | 1/2011 | | |
| WO | WO-2012127107 A1 * | 9/2012 | ............. | A01G 7/045 |

OTHER PUBLICATIONS

International Search Report and Written Opinion for related PCT application PCT/US2012/064198. International filing date Nov. 8, 2012.
(Continued)

*Primary Examiner* — Niketa Patel
*Assistant Examiner* — Sebastian X Lukjan
(74) *Attorney, Agent, or Firm* — Robert D. Buyan; Stout, Uxa & Buyan, LLP

(57) ABSTRACT

Battery powered light therapy systems capable of delivering 2-10 Joules per cm. sq. of light energy to a target treatment zone covering more than 700 sq. cm. of body surface area such that the light penetrates to a depth of 2 to 8 mm below a skin surface of the target treatment zone.

15 Claims, 9 Drawing Sheets

Related U.S. Application Data application No. 15/980,277, filed on May 15, 2018, now abandoned, which is a continuation of application No. 14/534,083, filed on Nov. 5, 2014, now Pat. No. 9,968,799, which is a continuation of application No. 13/672,554, filed on Nov. 8, 2012, now Pat. No. 8,900,283, application No. 18/118,988 is a continuation of application No. 17/187,370, filed on Feb. 26, 2021, now abandoned.

(60) Provisional application No. 61/557,319, filed on Nov. 8, 2011, provisional application No. 62/983,247, filed on Feb. 28, 2020.

(56) References Cited

U.S. PATENT DOCUMENTS

| | | | |
|---|---|---|---|
| 6,221,095 | B1 | 4/2001 | Zuylen et al. |
| 6,596,016 | B1 | 7/2003 | Vreman et al. |
| 6,743,249 | B1 | 6/2004 | Alden et al. |
| D497,882 | S | 11/2004 | Huang |
| D579,572 | S | 10/2008 | Wittenbrock et al. |
| D623,308 | S | 9/2010 | Kramer |
| D664,932 | S | 8/2012 | Sedic |
| D684,269 | S | 6/2013 | Wang et al. |
| 8,756,731 | B1 | 6/2014 | Huttner et al. |
| 8,900,283 | B2 | 12/2014 | Johnson et al. |
| D732,677 | S | 6/2015 | Kristensen et al. |
| D802,779 | S | 11/2017 | Inoue et al. |
| 9,968,799 | B2 | 5/2018 | Johnson et al. |
| D858,463 | S | 9/2019 | Nien et al. |
| D870,909 | S | 12/2019 | Sedic |
| D879,053 | S | 3/2020 | Yu |
| D879,341 | S | 3/2020 | Kassin et al. |
| D890,752 | S | 7/2020 | Huang et al. |
| D894,368 | S | 8/2020 | Lee |
| D925,046 | S | 7/2021 | Johnson |
| 2002/0143373 | A1 | 10/2002 | Courtnage et al. |
| 2003/0009205 | A1 | 1/2003 | Biel |
| 2004/0138726 | A1 | 7/2004 | Savage et al. |
| 2005/0110702 | A1 | 5/2005 | Aoki et al. |
| 2006/0217690 | A1 | 9/2006 | Bastin et al. |
| 2007/0129776 | A1 | 6/2007 | Robins et al. |
| 2007/0156208 | A1* | 7/2007 | Havell ................. A61N 5/0616 607/88 |
| 2007/0167999 | A1 | 7/2007 | Breden et al. |
| 2007/0208395 | A1* | 9/2007 | Leclerc ................ A61N 5/0616 607/86 |
| 2007/0208396 | A1 | 9/2007 | Whatcott et al. |
| 2007/0217199 | A1 | 9/2007 | Adam et al. |
| 2009/0105791 | A1 | 4/2009 | McGinnis et al. |
| 2010/0114007 | A1 | 5/2010 | Fischer et al. |
| 2010/0234927 | A1 | 9/2010 | Lin |
| 2010/0274329 | A1 | 10/2010 | Bradley et al. |
| 2010/0318161 | A1 | 12/2010 | Brawn |
| 2011/0077675 | A1 | 3/2011 | Rofougaran |
| 2011/0144724 | A1 | 6/2011 | Pryor et al. |
| 2011/0144727 | A1* | 6/2011 | Benedict .............. A61N 5/0613 607/91 |
| 2012/0253433 | A1 | 10/2012 | Rosen et al. |
| 2013/0274839 | A1 | 10/2013 | Johnson et al. |
| 2014/0128941 | A1 | 5/2014 | Williams |
| 2014/0128942 | A1 | 5/2014 | Bembridge et al. |
| 2016/0016001 | A1 | 1/2016 | Loupis et al. |
| 2018/0243582 | A1 | 8/2018 | Kaneda et al. |
| 2019/0373687 | A1 | 12/2019 | Williams et al. |

OTHER PUBLICATIONS

Definition of flexible. Merriam-Webster Dictionary, retrieved on Dec. 13, 2013; Retrieved from the internet: <http://www.merriam-webster.com/dictionary/flexible>.

Definition of deform. Merrima-Webster Dictionary, retrieved on Dec. 13, 2013; Retrieved from the internet: <http://www.merrima-webster.com/dictionary/deform>.

Daniel Barolet, M.D. "Light-Emitting Diodes (LEDs) in Dermatology", Seminars in Cutaneous Medicine and Surgery, vol. 27, pp. 227-238, 2008.

Daniel Barolet, et al., Importance of Pulsing Illumination Parameters in Low-Level-Light Therapy, Journal of Biomedical Optics, vol. 15, No. 4, pp. 048005-1-048005-8, 2010.

Supplementary European Search Report dated Jul. 23, 2015 for related European Application No. 12847625.6.

PCT International Search Report dated Sep. 11, 2020 in related PCT Application No. PCT/US2020/037586.

Biophotas, Inc. Introduces the Celluma POD Light Therapy Device—News Provided by BioPhotas, Inc., May 31, 2018. https://www.prnewswire.com/news-releases/biophotas-inc-introduces-the-celluma-pod-light-therapy-device-300657659.html.

PCT International Search Report dated May 24, 2021 in related PCT Application No. PCT/US2021/020023.

Extended European Search Report dated May 25, 2023 in related European Application No. 20822634.0.

* cited by examiner

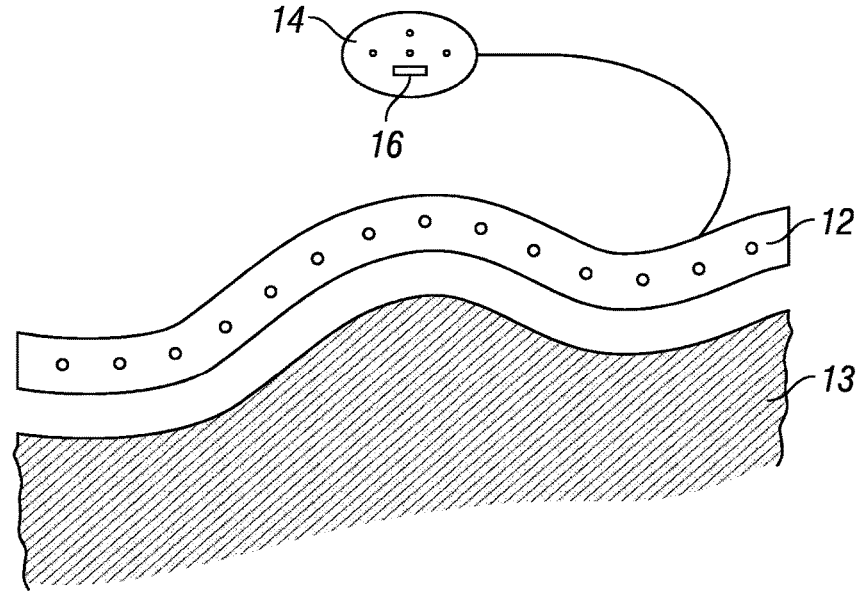
FIG. 1
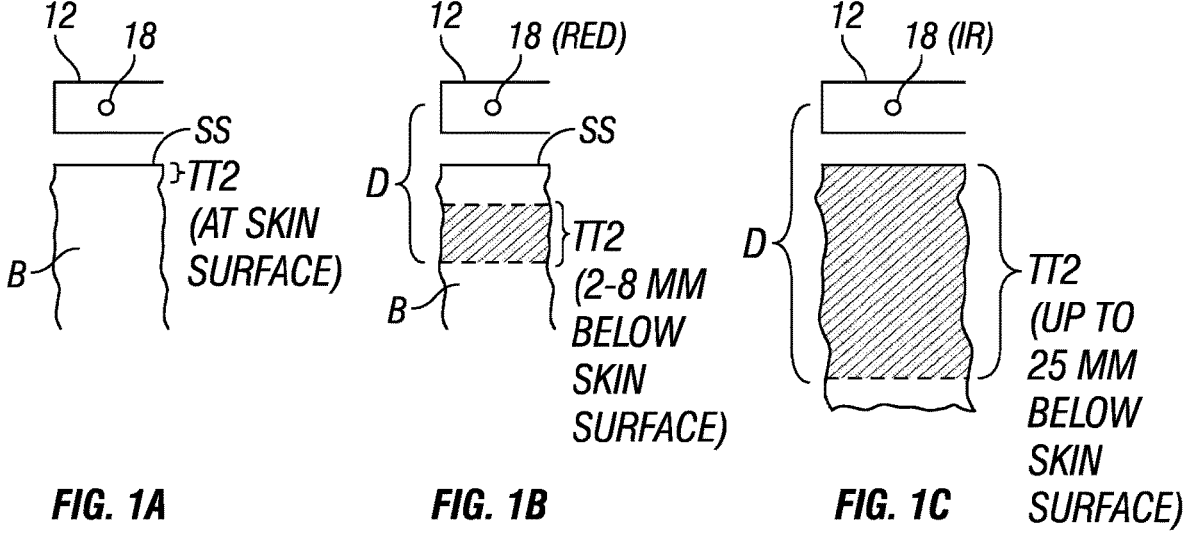
FIG. 1A          FIG. 1B          FIG. 1C

*14*

*14*

BATTERY POWERED SYSTEMS FOR LIGHT THERAPY AND RELATED METHODS

RELATED APPLICATIONS

This is: a) a continuation-in-part of copending U.S. patent application Ser. No. 17/162,966 entitled Shapeable Light Therapy Device and Method filed Jan. 29, 2021, which is a continuation of U.S. patent application Ser. No. 15/980,277 filed May 15, 2018 and now abandoned, which is a continuation of U.S. patent application Ser. No. 14/534,083 entitled Shapeable Light Therapy Device and Method filed Nov. 5, 2014 and issued May 15, 2018 as U.S. Pat. No. 9,968,799, which is a continuation of U.S. patent application Ser. No. 13/672,554 entitled Shapeable Light Therapy Device and Method filed Nov. 8, 2012 and issued Dec. 2, 2014 as U.S. Pat. No. 8,900,283, which claims priority to U.S. Provisional patent Application No. 61/557,319 entitled Shapeable Light Therapy Device and Method filed Nov. 8, 2011 and b) a continuation of copending U.S. patent application Ser. No. 17/187,370 entitled Battery Powered Systems for Light Therapy and Related Methods filed Feb. 26, 2021 which claims priority to U.S. Provisional Patent application No. 62/983,247 entitled Battery Powered Systems for Light Therapy and Related Methods filed Feb. 28, 2020, the entire disclosure of each such patent and application being expressly incorporated herein by reference.

FIELD OF THE INVENTION

The present invention relates generally to the fields of physics, electronics, biology and medicine and more particularly to devices and methods for delivering light therapy to humans or animals.

BACKGROUND

Light therapy (i.e., "phototherapy"), using various types of light, has been used or proposed for use in a number of cosmetic and therapeutic applications, including but not necessarily limited to improvement of skin elasticity, deterrence of skin aging, treatment of dermatological disorders (e.g., acne, psoriasis), healing of wounds, treatment of jaundice in newborns, and treatment of certain psychological conditions such as seasonal affective disorder (SAD) and certain sleep disorders. In some applications, light therapy is used alone while in others it is used in combination with drugs or agents (e.g., photo-sensitizing agents, photo-activating agents, agents which reduce skin opacity or improve light penetration through or into the skin, etc.).

Applicant is the owner of related U.S. Pat. No. 8,900,283 (Johnson) and U.S. Pat. No. 9,968,799 (Johnson), the entire disclosures of which are expressly incorporated herein by reference.

SUMMARY

The present invention provides new light therapy systems and methods wherein a light emitting device comprising a light emitting pad member is sized and configured to extend over at least part of a subject's body. In some embodiments the light emitting pad may be configured to extend over all, substantially all or more than half of the subject's body.

In accordance with one aspect of the invention, there is provided a shape retaining, light emitting pad device for delivering light therapy to a human body part comprising: a deformable shape-retaining member which extends around a central aperture (i.e., an open area); flexible light emitting circuitry; a front shield or barrier; a rear flexible member; and a power source; wherein: the flexible light emitting circuitry is positioned in the central open area of the deformable shape retaining member such that the deformable shape retaining member surrounds the flexible light emitting circuitry; the front shield or barrier is positioned on a front side of the flexible light emitting circuitry, said front shield or barrier comprising a translucent material which allows light emitted by flexible light emitting circuitry to pass through the front barrier or shield; the rear flexible member is positioned on a rear side of the flexible light emitting circuitry; the shape of the device can be modified by a user a user can hand-shape the device into a modified configuration which conforms to a shape of the human body part thereby causing bending or deformation of the shape retaining member, which then causes the device to retain that modified configuration; and the device is positionable with the front shield or barrier in juxtaposition to said body part so that light emitted from the flexible light emitting circuitry passes through the translucent material of the front shield or barrier and onto said body part, thereby delivering light therapy to said body part.

Further in accordance with the present disclosure, the tight therapy system may be configured such that the battery delivers sufficient power to the light emitter(s) to cause the light emitter(s) to deliver 2 to 10 Joules per cm. sq. of light energy to a penetration depth of up to 25 mm below a skin surface covering a target treatment zone. The target treatment zone may cover an area that exceeds: 100 square centimeters, or 200 square centimeters, or 300 square centimeters, or 400 square centimeters, or 500 square centimeters, or 600 square centimeters, or 700 square centimeters of body surface area, or the size of the target treatment zone may vary (e.g., by using pads of differing size) within a range defined by any two of the preceding values. In one embodiment the pad member and light emitter(s) are configured to deliver light to a target treatment zone that covers 718.5 square centimeters of skin or body surface area.

Further in accordance with the present disclosure, the light emitter(s) may comprise red LEDs and the system may be configured such that the battery delivers sufficient power to the red LEDs to cause the red LEDs to deliver 2-10 Joules per cm. sq. of red light to a target treatment zone that covers more than 700 sq. cm. of body surface area such that the red light penetrates to a depth of 2 to 8 mm below a skin surface of the target treatment zone.

Still further in accordance with the disclosure, there are provided methods for using the above-summarized light therapy systems to deliver light therapy to the bodies of humans or other animals.

Additional aspects and details of the light therapy system and associated methods will be understood upon reading of the detailed description and examples set forth herebelow.

BRIEF DESCRIPTION OF THE DRAWINGS

The following figures are included in this provisional patent application and referenced in the following description and claim statements. These figures are intended only to illustrate certain aspects or embodiments of the disclosed system and are not limiting in any respect.

FIG. 1 is a schematic diagram showing one embodiment of a system of the present disclosure.

FIG. 1A is a schematic diagram showing an example of a target treatment zone for blue light therapy in accordance with the present disclosure.

FIG. 1B is a schematic diagram showing an example of a target treatment zone for red light therapy in accordance with the present disclosure.

FIG. 1C is a schematic diagram showing an example of a target treatment zone for near infrared light therapy in accordance with the present disclosure.

DETAILED DESCRIPTION

Figure 2:
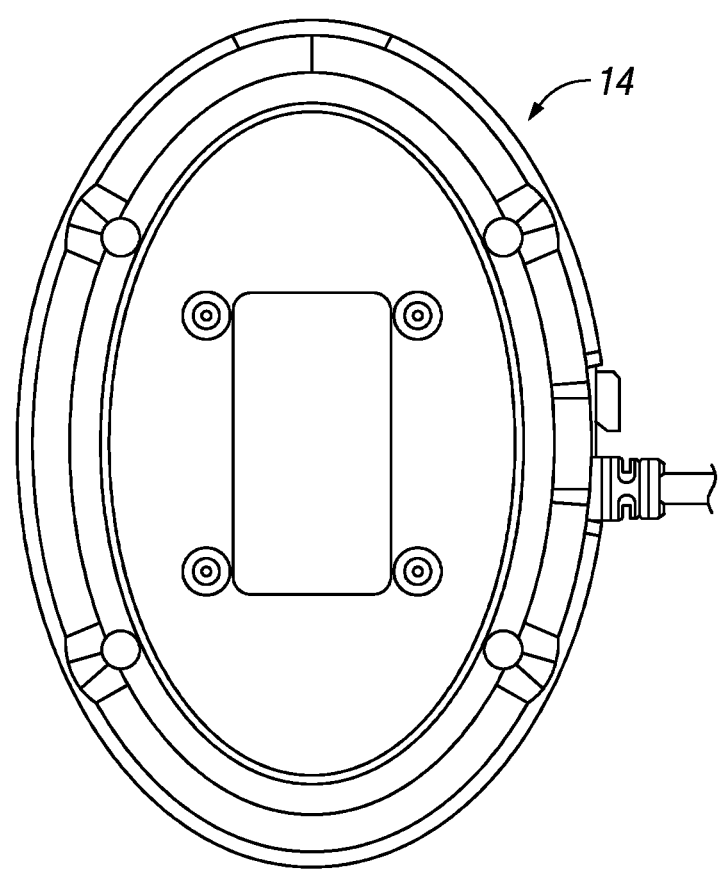
FIG. 2 is a bottom view of a controller/user interface in accordance with the present disclosure.
Figure 3:
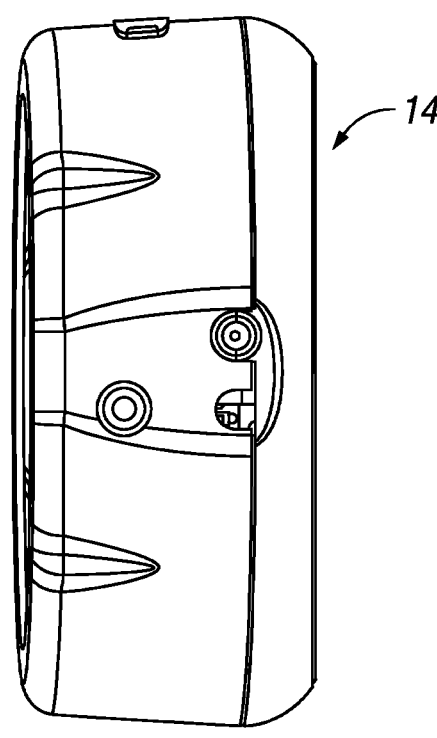
FIG. 3 is a front view of a controller/user interface in accordance with the present disclosure.
Figure 4:
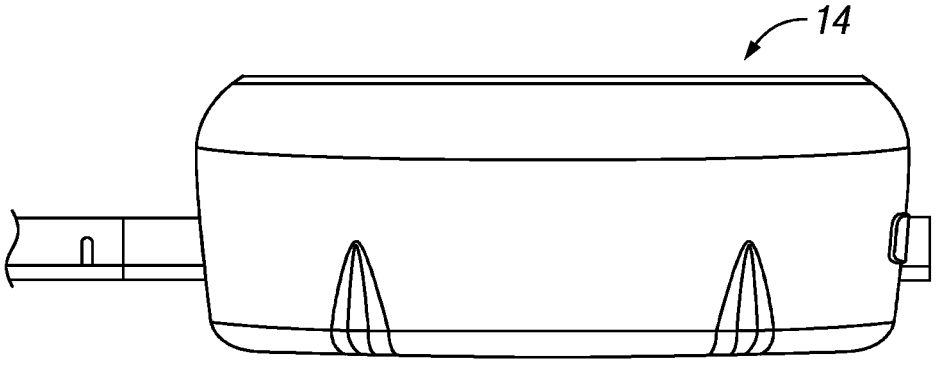
FIG. 4 is a left side view of a controller/user interface in accordance with the present disclosure.
Figure 5:
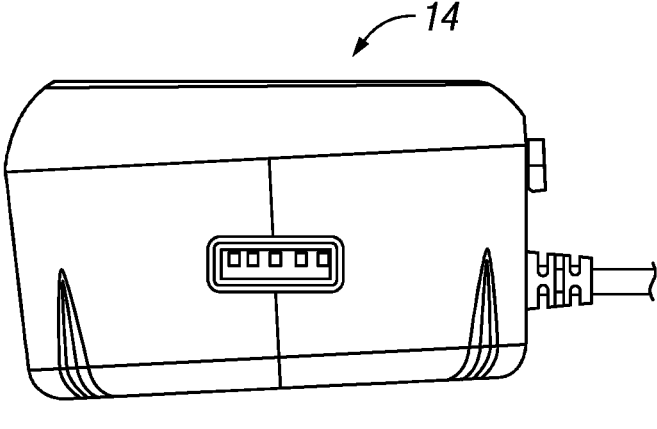
FIG. 5 is a right side view of a controller/user interface in accordance with the present disclosure.
Figure 6:
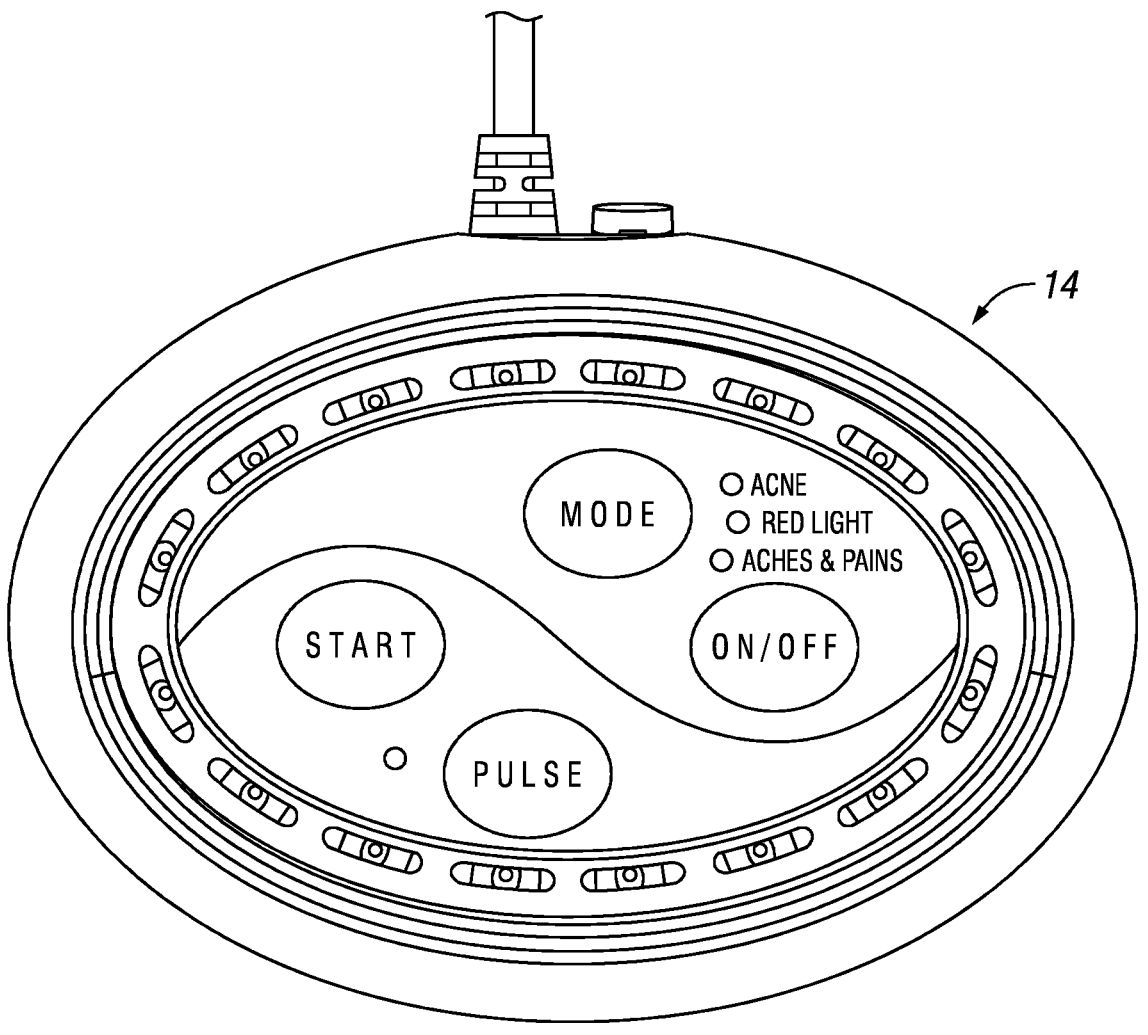
FIG. 6 is a top view of a controller/user interface in accordance with the present disclosure.

As used in this provisional patent application the term "pad member" is to be interpreted broadly and shall include any suitable structure including, but not necessarily limited to, flexible flat or planar structures, pads, mats, panels, sheets, blankets, etc. Light emitters, such as light emitting diodes (LEDs), emit light from one side (i.e., a light-emitting side) of the pad. The pad may be positioned under or over the body of a subject such that light which emanates from the light-emitting side of the pad is cast on the subject body thereby providing light therapy. Optionally, the pad may be flexible and one or more shapeable member(s) may be positioned on or in region(s) of the pad to render such region(s) of the pad formable into shape(s) which conform to a body part of the subject or which facilitate placement on or in abutment with an underlying or adjacent surface.

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

FIG. 1 is a schematic diagram of a system 10 of the present invention positioned to provide light therapy to a portion of a human body B. This system 10 includes at least one shapeable light emitting pad 12 having light emitters 18 and a controller/user interface 14 and a battery 16. The battery 16 may be housed within the controller/user interface 14. The pad 12 is preferably formable into a plurality of retained shapes so that the shape of the pad 12 may correspond to various curved body surfaces so that the light emitters 18 are within a desired distance D of a target treatment zone TTZ such that the light which reaches the target treatment zone TTZ is of sufficient intensity to cause increased uptake of ATP in cells within the target treatment zone TTZ. Clinical data indicates that delivering 2-10 Joules per cm. sq. will trigger the up-regulation of ATP at a particular target treatment zone TTZ. The following Table 1 below and FIGS. 1A, 1B and 1C show target treatment zones TTZs for red, blue and near infrared LED light emitters 18.

| Light | Wavelength (nM) | Target Treatment Zone (TTZ) |
|---|---|---|
| Blue | at or approximately 460 | At the skin surface |
| Red | 640 | 2 to 8 mm below the skin surface |
| Near infrared | 880 | Up to 25 mm below the skin surface. |

The wavelengths shown in Table 1 may vary. For example, such wavelengths bay vary +/− 5 nM. Alternatively, such wavelengths may vary +/=10 nM. Alternatively, such wavelengths may be "approximate," meaning that the specified wavelength may vary by any amount that does not render the light ineffective for its stated therapeutic purpose.

The battery 16 is capable of providing sufficient power to cause each light emitter 18 to emit light from the pad 12, over the desired distance D so that light energy of 2-10 Joules per square centimeter of will reach the target treatment zone TTZ for that type of light emitter 18. The delivery of this dosage of light therapy results in upregulation of ATP in cells within that target treatment zone TTZ. A battery useable in this system may draw <200 uA in standby Minimum Voltage 4.8V Charge Voltage 8.438V Max Charge Current 2.046 A Capacity>=6120 mAh Impedance<206 mOhms fully charged Blade connector is not keyed. Typical pinout has Pin 1 as battery positive.

As illustrated in FIG. 1A, for light emitters 18 which emit blue light, the battery 16 will provide sufficient power to cause blue light to travel a distance D from the blue light emitters 18 to a target treatment zone TTZ located at the skin surface SS such that 2 to 10 Joules per cm. sq. of blue light energy is delivered within that target treatment zone TTZ (the skin surface).

As illustrated in FIG. 1B, for light emitters 18 that emit red light, the battery 16 will provide sufficient power to cause red light to travel a desired distance D from the red light emitters 18 to a target treatment zone TTZ that is 2 to 8 mm below the skin surface such that 2-10 Joules per cm. sq. of red light energy is delivered within that target treatment zone TTZ (2 to 8 mm below the skin surface.)

As illustrated in FIG. 1C, for light emitters that emit near infrared light, the battery 16 will provide sufficient power to cause near infrared light to travel a desired distance D from the near infrared light emitters to the target treatment zone (up to 25 mm below the skin surface) such that 2-10 Joules per cm. sq. of near infrared light energy is delivered within that target treatment zone TTZ (up to 25 mm below the skin surface).

One type of battery that is suitable for use in a system 10 that includes blue, red and near infrared light emitters 18 is a 4 cell, 7.2 volt, 6.8 Amp hour lithium ion battery. The voltage is stepped up to 12V.

In some embodiments the pad 12 may be place in contact with the skin surface, while in other embodiments, the pad 12 may remain a spaced distance away from the skin surface. In either event the light emitters 18 will be within the desired distance D of the target treatment zone TTZ for that type of light emitter 18. The pad 12 may be formable into, and will retain without a strap or other retaining member, a plurality of different shapes, each of which has a plurality of curves (i.e., "multi-curvate" shapes). In this manner, the pad 12 may be pre-shaped to conform to the configuration of a body portion to the treated so that, when the pad 12 is placed on or near that body portion, all of substantially all of the pad's light emitters 18 will be within the desired distance D of the target treatment zone TTZ.

Figure 7:
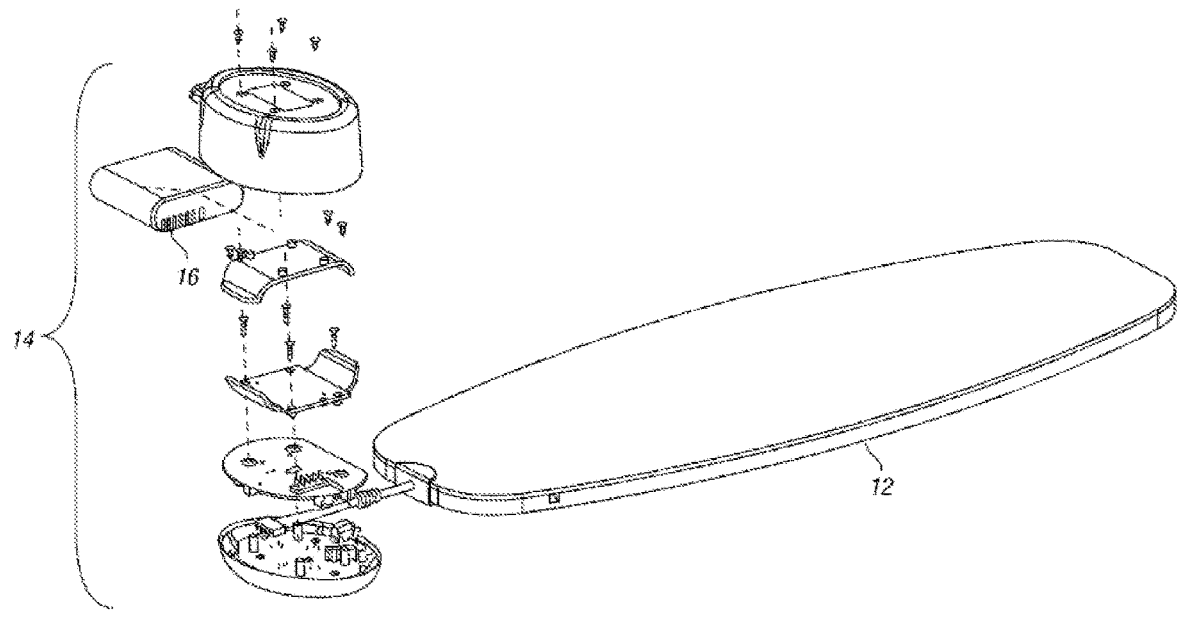
FIG. 7 shows an embodiment of a light therapy system comprising a shape-retaining light emitting pad and a controller/user interface, with the controller/user interface component being shown in exploded format.
Figure 7A:
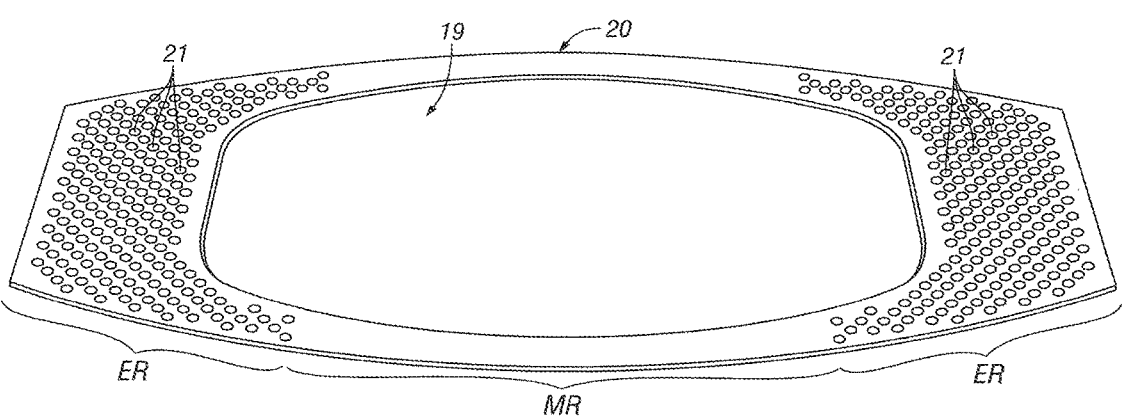
FIG. 7A shows a plastically deformable component used in the shape retaining light emitting pad of the light therapy system shown in FIG. 7.
Figure 7B:
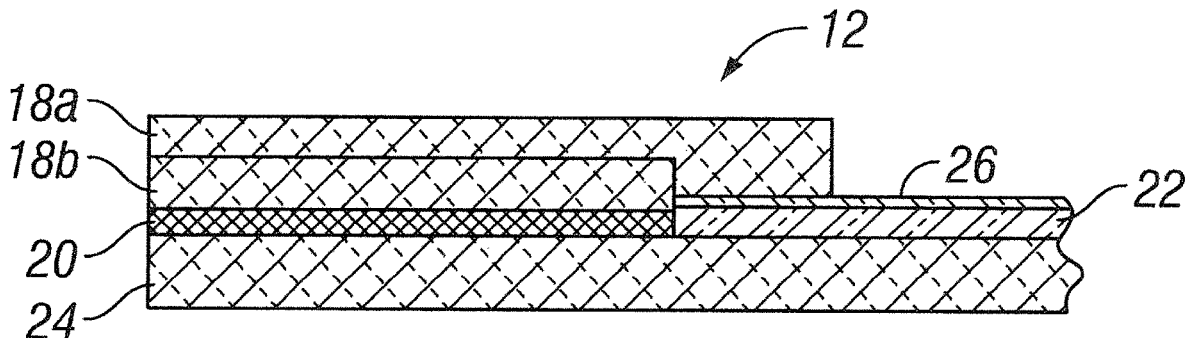
FIG. 7B is a partial cross sectional view of the shape-retaining light emitting pad of the light therapy system shown in FIG. 7.
Figure 8:
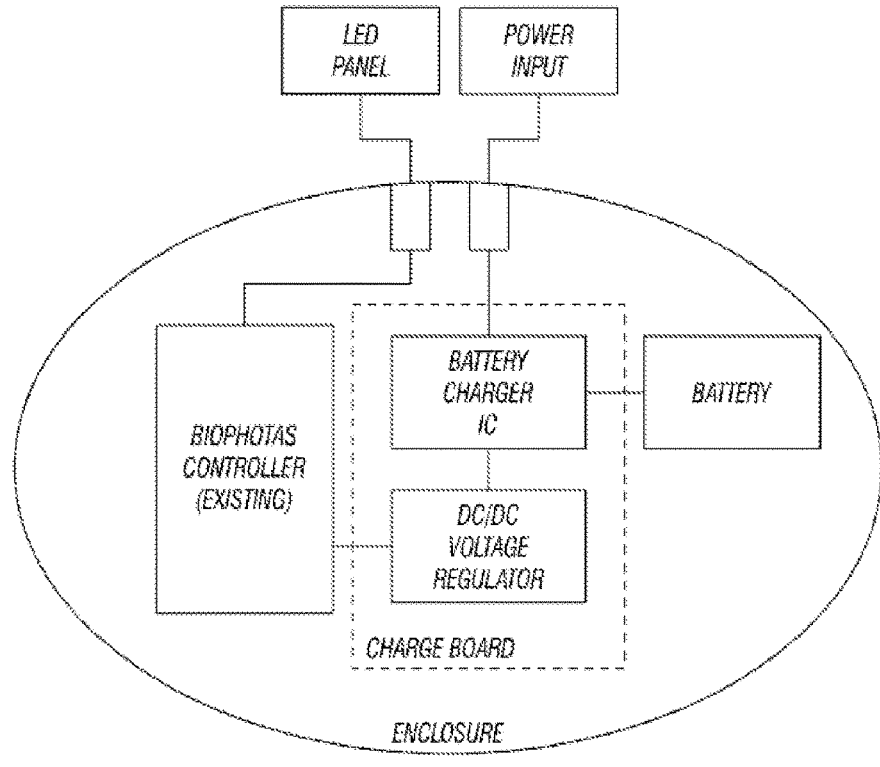
FIG. 8 is an electrical block diagram of a light therapy system according to the present disclosure.

The pad 12 may be constructed as described in Applicant's above-incorporated U.S. patent application Ser. No. 17/162,966 entitled Shapeable Light Therapy Device and Method, of which this application is a continuation-in-part, and from which FIGS. 7A and 7B of this application are reproduced. FIG. 7A shows a shape-retaining member 20n which is one of the components of the pad 12. FIG. 7B shows a cross sectional view of the assembled pad 12.

As shown in FIG. 7A, the shape retaining member 20 surrounds a central aperture (i.e., open area) 19, and has a mid-region MR as well as end regions E. The shape retaining member 20 is formed of a plastically deformable material (e.g., aluminum or other suitable metal, deformable memory plastic, etc.) that is flexible enough to be deformed to a desired configuration by hand while also having sufficient shape memory to retain the configuration to which it has been deformed during subsequent use of the device for delivery of a light therapy session.

As seen in FIG. 7B, the component parts of the pad 12 include, the shape retaining member 20 having a central aperture or open area 19 (fully shown in FIG. 7A), flexible LED circuitry 22 positioned in the central open area 19 of the shape retaining member 20, a rear flexible pad layer 24, and a front shield or barrier 26. Additionally, a front flexible pad layer 18, which may be formed of two layers of flexible plastic foam 18a and 18b, is positioned on the front side of the shape retaining member 20. The flexible LED circuitry layer 22 may comprise one or more flexible LED circuit boards having a plurality of light emitters. Specifically, in this example, the flexible circuitry layer 22 may comprise a flexible printed circuit board having the LEDs and possibly other components such as resistors. The shield or barrier 26 extends over the front of the flexible LED circuitry layer 22, thereby preventing the LEDs and any other electronic components on the flexible circuitry layer 22 from directly contacting objects or body surfaces and/or to allow hygienic cleansing of the device, The shield or barrier comprises translucent material which allows light emitted from the flexible LED circuitry layer 22 to pass through the shield or barrier 26.

In embodiments where a portion of the pad 12 directly contacts the skin surface SS, the skin-contacting portion of the pad 12 may comprise a translucent panel through which the light is cast from the light emitters 18. Such skin-contacting translucent panel may be formed of material that can be sanitized after each use. Alternatively, such translucent panel may be covered with a disposable barrier layer, such as a clear plastic film, that may be peeled away and discarded after each use. In such embodiments, the light emitters 18 may be positioned within the pad 12 so that, when the translucent panel is in contact with the subject's skin, the light emitters 18 will be nominally ⅓ of a centimeter from the surface of the skin. This close emission proximity is designed to leverage the Inverse Square Law that states that as the distance between a light emitter 18 and a surface of absorption (the skin) is doubled the energy available for absorption decreases by 4 times. In application, this means the closer to the skin surface SS the light emitters 18 are positioned, the less power required from the battery 16 to deliver a desired therapeutic dose of light energy (e.g., 2-10 Joules per cm. sq.) to the target treatment zone TTZ. Pads 12 of varied sizes may be used. The herein described system is capable of operating with a pad 12 sized to deliver 2 to 10 (e.g., up to 10) Joules per cm. sq. of light energy (e.g., red light) to a depth of 2 to 8 mm (e.g., up to 8 mm) below the skin surface over a target treatment zone TTZ covering more than 700 square centimeters (e.g., 718.5 square centimeters) of body surface area.

In some embodiments, the system 10 may be programmed to deliver light therapy in a plurality of alternative light treatment modes intended for different therapeutic or cosmetic applications, including a) one light treatment mode wherein the emitted light is primarily near infrared; b) another light treatment mode wherein the emitted light is primarily red; and c) yet another light treatment mode wherein the emitted light is primarily blue. Operation of the device 10 in the near infrared treatment mode may cause the LEDs to emit light having a wavelength of, or of about, 880 nm. Operation of the device 10 in the red treatment mode may cause the LEDs to emit light having a wavelength of, or of about, 640 nm. Operation of the device 10 in the blue treatment mode may cause the LEDs to emit light having a wavelength of, or of about, 465 nm. As explained above, these different treatment modes may be selected depending on the pathological or cosmetic condition being treated and/or the depth of light penetration desired. See, Bartolet, D., Light-Emitting Diodes (LEDs) in Dermatology; Seminars in Cutaneous Medicine and Surgery, Vol. 27: pp. 227-238 (2008).

The controller/user interface 14 may include a switch for turning the power on/off and a selector for selecting which treatment mode is desired. Also, optionally, the treatment times may be fixed or the user interface may include a timer set for setting the desired treatment time. Also, optionally, the device may be programmed to emit light in each treatment mode in either a pulsed (e.g., modulated) or non-pulsed fashion and the user interface may include a switch or function to allow the user to select or not select whether pulsing (e.g., modulation) is desired. For example, the device 10 may be sent to default to a pulsed delivery of light in each treatment mode unless the user inputs a signal through the user interface 14 to terminate the pulsing. More specifically, in this non-limiting example, when a light therapy session is initiated with the device set in the one treatment mode, the blue LEDs will emit blue light at a 1% duty cycle and the red and near infrared LEDs will fade up from 1% to 90% in 20 seconds. When a light therapy session is initiated with the device set in another treatment mode, the blue LEDs will fade up from 1 to 90% in 20 seconds and the red and near infrared LEDs will fade up from 1.3% to 2.5% in 2.5 seconds. Also, when a light therapy session is initiated with the device set in yet another treatment mode, the blue LEDs will fade up from 1% to 90% in 20 seconds and the red and near infrared LEDs will cycle from 30% to 80% in 11.5 seconds. In this particular non-limiting example, each treatment mode will deliver pulsed light unless pulsation is turned off via the user interface 14, as follows: a) the first light treatment mode will deliver light at a pulse width modulation frequency of about 680 Hz unless pulse width modulation is turned off via the user interface 14; b) the second light treatment mode delivers light at a pulse width modulation frequency of about 800 Hz unless pulse width modulation is turned off via the user interface 14 and the third light treatment mode delivers light at a pulse width modulation frequency of about 80 Hz unless pulse width modulation is turned off via the user interface 14. As explained above, this ability to select the desired modulation (e.g., pulsation or non-pulsation) allowed the system 10 to be used to achieve different therapeutic effects. See, Barto-let, D., Importance of Pulsing Illumination Parameters in Low-Level-Light Therapy; Journal of Biomedical Optics, Vol. 15, No. 4: pp. 048001-048005 (2010).

Figure 9:
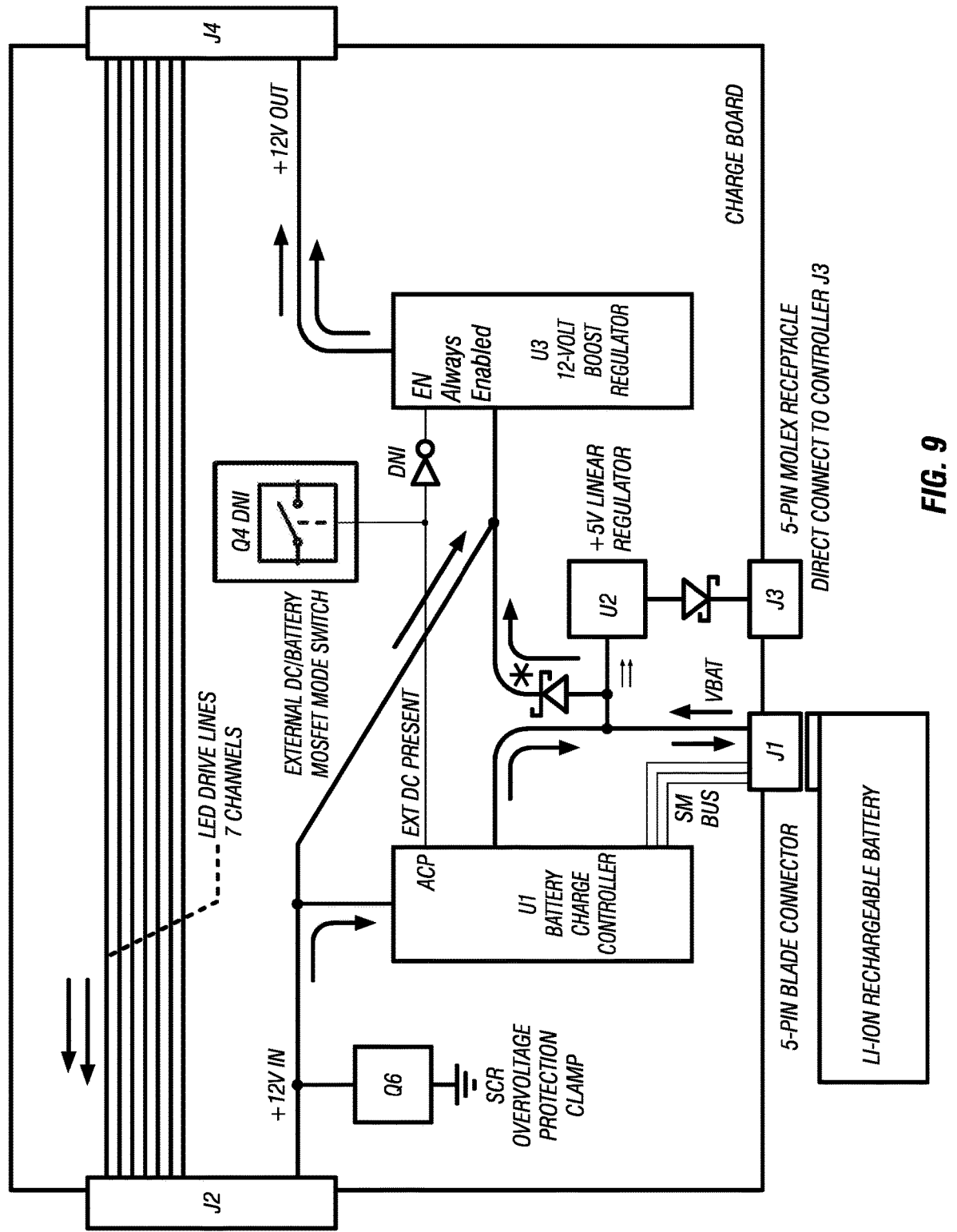
FIG. 9 is a detailed block diagram of a charge board component of a light therapy system according to the present disclosure.
Figure 10:
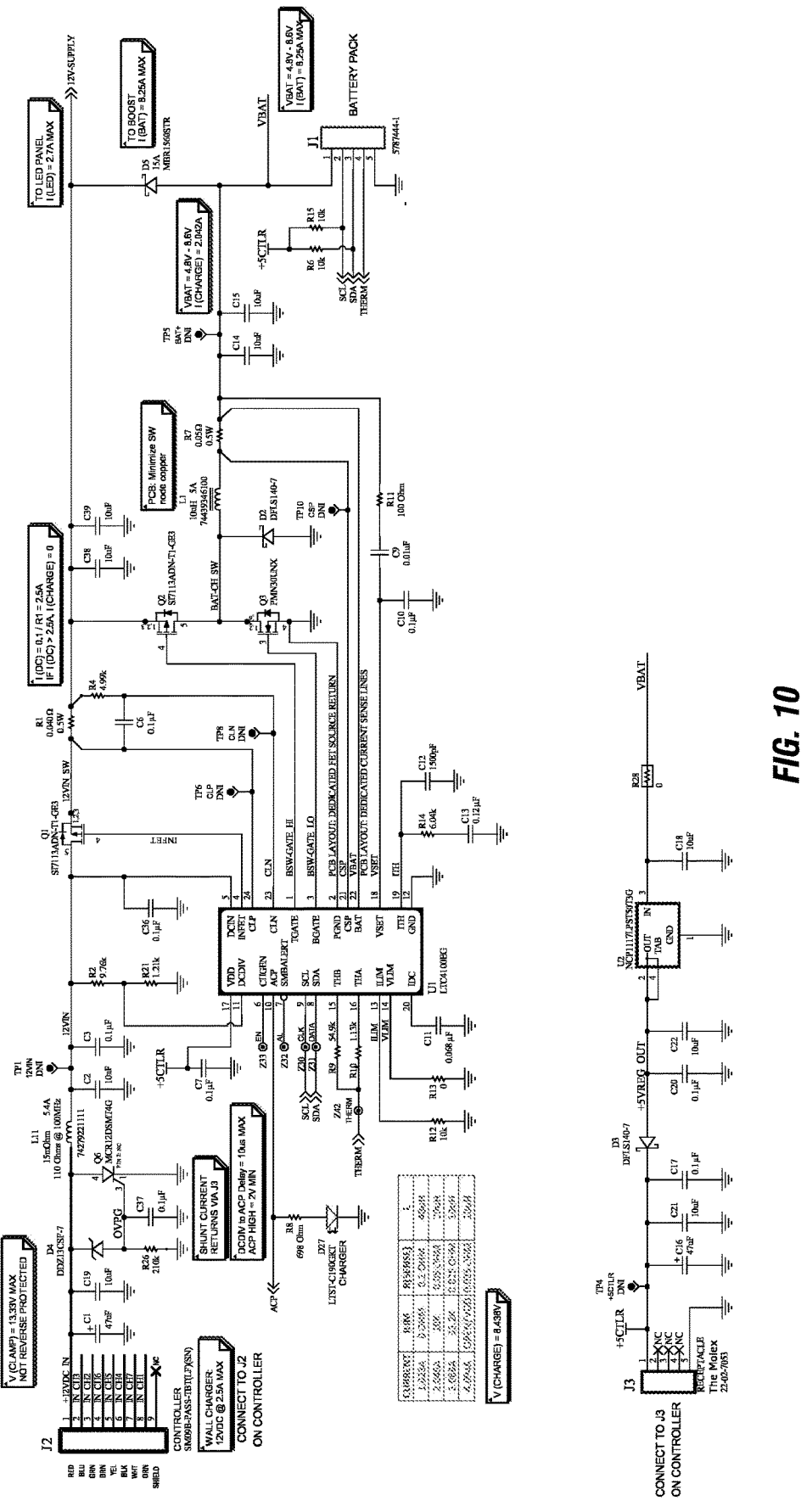
FIG. 10 is an electrical schematic showing power input and battery portions of a charge board component of a light therapy system according to the present disclosure.
Figure 11:
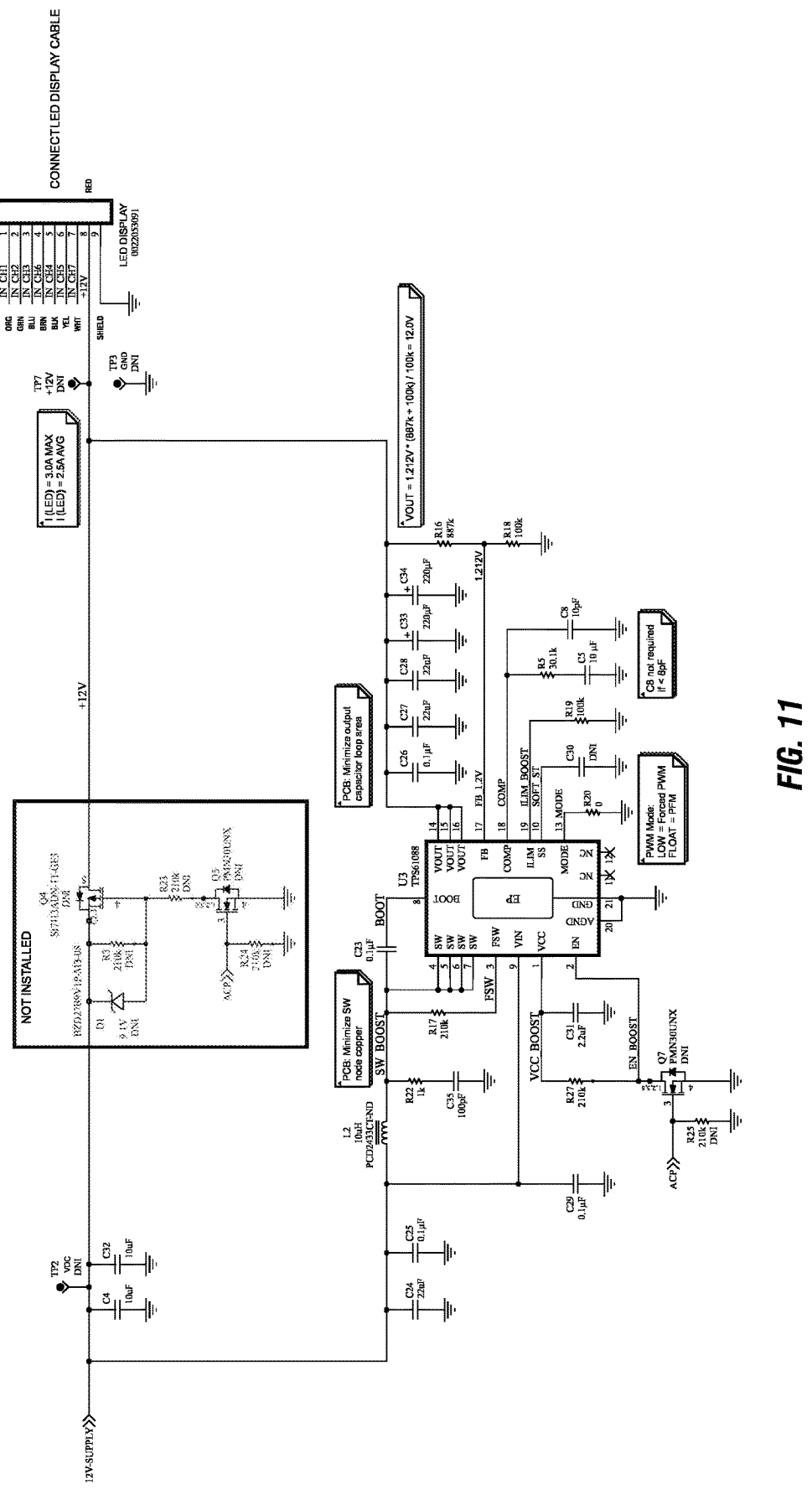
FIG. 11 is an electrical schematic showing boost regulation and output portions of a charge board component of a light therapy system according to the present disclosure.

FIGS. 9 thorough 11 show additional details of a the battery controller and charge board.

In some embodiments the controller/user interface 14 may include a display. Such display may display indications of whether the power is on or off and what light treatment mode has been selected. Optionally, such display may also display a treatment time that has been selected and/or elapsed and/or remaining; and, optionally, whether pulse width modulation is on or off.

In some embodiments, the controller/user interface may also be useable to switch between a pulsed mode and a non-pulsed mode as described in the above-incorporated U.S. Pat. No. 8,900,283 (Johnson) and U.S. Pat. No. 9,968, 799 (Johnson).

Although the invention has been described hereabove with reference to certain examples or embodiments of the invention, various additions, deletions, alterations and modi-fications may be made to those described examples and embodiments without departing from the intended spirit and scope of the invention. For example, any elements, steps, members, components, compositions, reactants, parts or portions of one embodiment or example may be incorpo-rated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, mem-bers, components, compositions, reactants, parts or portions of any invention or example described herein may optionally exist or be utilized in the absence or substantial absence of any other element, step, member, component, composition, reactant, part or portion unless otherwise noted. All reason-able additions, deletions, modifications and alterations are to be considered equivalents of the described examples and embodiments and are to be included within the scope of the following claims.

What is claimed is:

1. A shape retaining, light emitting pad device for deliv-ering light therapy to a treatment area on a human body, said device comprising:
   a deformable shape-retaining member which extends around a central open area;

flexible light emitting circuitry layer comprising one or more flexible circuit boards positioned in axial align-ment with the central open area of the deformable shape retaining member;
   a front shield or barrier;
   a rear flexible member; and
   a power source comprising a rechargeable battery;
   wherein:
   the front shield or barrier is positioned on a front side of the flexible light emitting circuitry, said front shield or barrier comprising a translucent material which allows light emitted by flexible light emitting circuitry to pass through the front barrier or shield; and
   the rear flexible member is positioned on a rear side of the flexible light emitting circuitry;
   the shape of the device can be hand-shaped into a modi-fied configuration which conforms to a shape of the human body part thereby causing bending or deforma-tion of the shape retaining member, which thereafter causes the device to retain that modified configuration; and
   the device is positionable with the front shield or barrier in juxtaposition to said treatment area so that light emitted from the flexible light emitting circuitry passes through the translucent material of the front shield or barrier and onto said treatment area.

2. A device according to claim 1 wherein the deformable shape retaining member comprises a malleable metal.

3. A device according to claim 1 wherein the deformable shape retaining member comprises a shape retaining plastic.

4. A device according to claim 1 wherein the flexible light emitting circuitry comprises light emitting diodes.

5. A device according to claim 4 wherein at least some of the light emitting diodes emit blue light.

6. A device according to claim 4 wherein at least some of the light emitting diodes emit red light.

7. A device according to claim 4 wherein at least some of the light emitting diodes emit infrared light.

8. A device according to claim 1 wherein, when operating solely on power provided by the rechargeable battery, the device delivers 2-10 Joules per square centimeter of light energy to the treatment area.

9. A device according to claim 8 wherein the size of the treatment area is more than 700 cm. sq.

10. A device according to claim 9 wherein the device delivers said 2 to 10 Joules per cm. sq. of light energy to a depth of 25 mm below a skin surface covering said treatment area.

11. A device according to claim 1 wherein the flexible light emitting circuitry comprises blue, red and near infrared light emitters.

12. A device according to claim 11 further comprising a controller useable for causing the device to alternately operate in in a plurality of light treatment modes.

13. A device according to claim 12 wherein the plurality of light treatment modes comprises:
   a first mode wherein primarily or entirely blue light is emitted;
   a second mode wherein primarily or entirely red light is emitted; and
   a third mode wherein primarily or entirely near infrared light is emitted.

14. A method for using a device according to claim 1, said method comprising the steps of:

forming the device into a curved shape whereby causing bending or deformation of the shape retaining member, which then causes the device to retain that curved configuration; and positioning the front shield or barrier in juxtaposition to said treatment area; and operating the device solely on power provided by the rechargeable battery to cause the flexible light emitting circuitry to emit light which passes through the translucent material of the front shield or barrier and onto said treatment area.

15. A method according to claim 14 wherein said operating of the device solely on power provided by the rechargeable battery delivers 2 to 10 Joules per cm. sq. of light energy to a depth 25 mm below a skin surface covering said treatment area.

* * * * *